(12) United States Patent
Adolfsen et al.

(10) Patent No.: US 6,348,354 B1
(45) Date of Patent: Feb. 19, 2002

(54) METHOD AND APPARATUS FOR CONTROLLING A STREAM OF LIQUID TEST PACKAGES IN A CAPSULE CHEMISTRY ANALYSIS SYSTEM

(75) Inventors: Robert Adolfsen, Montrose; Paul Gherson, Yorktown Heights, both of NY (US); David Lightbody, Cresskill, NJ (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/111,162

(22) Filed: Jul. 6, 1998

(51) Int. Cl.[7] ............................ G01N 35/08; G01N 1/10; G01N 21/00; B01L 11/00; G05B 1/00
(52) U.S. Cl. ............................ 436/53; 436/52; 436/54; 436/180; 422/63; 422/81; 422/103; 422/105; 422/108
(58) Field of Search .............................. 436/43, 50, 52, 436/53, 54, 180; 422/63, 81, 82, 103, 105, 108

(56) References Cited

U.S. PATENT DOCUMENTS

| | | | | |
|---|---|---|---|---|
| 3,759,667 A | * | 9/1973 | Bannister et al. | 422/81 |
| 3,909,136 A | * | 9/1975 | Thomas | 356/181 |
| 3,929,413 A | * | 12/1975 | Young et al. | 422/81 |
| 4,130,394 A | * | 12/1978 | Negersmith | 422/58 |
| 4,253,846 A | * | 3/1981 | Smythe et al. | 422/82 |
| 4,259,291 A | * | 3/1981 | Smythe | 422/82 |
| 4,328,185 A | * | 5/1982 | Reasons et al. | 422/82 |
| 4,517,302 A | * | 5/1985 | Saros | 436/180 |
| 5,268,147 A | | 12/1993 | Zabetakis et al. | 422/82 |
| 5,399,497 A | | 3/1995 | Kumar et al. | 436/53 |
| 5,466,946 A | | 11/1995 | Kleinschmitt et al. | 250/577 |

* cited by examiner

Primary Examiner—Jill Warden
Assistant Examiner—Brian R. Gordon
(74) Attorney, Agent, or Firm—Andrew L. Klawitter; John M. Paolino

(57) ABSTRACT

A method and apparatus for controlling a stream of liquid and air segments wherein the liquid and air segments are selectively aspirated into a first fluid conduit in a plurality of cycles, each cycle beginning with the aspiration of a first air segment and ending with the aspiration of a final air segment. The liquid and air segments are then transferred from the first fluid conduit to a second fluid conduit. The volume of the final air segment of each cycle is then adjusted after the final air segment has moved into the second fluid conduit. Next, the liquid segments and the air segments of each cycle are transferred from the second fluid conduit to a third fluid conduit. The volume of the first air segment of each cycle is then adjusted after the first air segment has moved into the third fluid conduit.

16 Claims, 12 Drawing Sheets

METHOD AND APPARATUS FOR CONTROLLING A STREAM OF LIQUID TEST PACKAGES IN A CAPSULE CHEMISTRY ANALYSIS SYSTEM

FIELD OF THE INVENTION

The present invention relates to a capsule chemistry sample liquid analysis system adapted for the automated clinical analysis of pluralities of human biological sample liquids, in particular to a method and apparatus for controlling a stream of liquid test packages flowing through such a system.

BACKGROUND

U.S. Pat. No. 5,268,147 (the "'147 patent") and U.S. Pat. No. 5,399,497 (the "'497 patent"), owned by the assignee hereof, the disclosures of which are incorporated herein by reference, describe a capsule chemistry sample liquid analysis system which operates through repeated reversible, bi-directional flow of an appropriately configured stream of liquid test packages, each test package consisting of alternating segments of a liquid, such as a sample, reagent or buffer, and air, to enable repeated, precisely timed analysis of the sample of each of the test packages in the stream by one or more sample liquid analysis means. As described in the '147 and '497 patents, the system generally comprises a sample liquid test package metering and supply means which operates to meter successive test packages for reaction and analysis within the system; a reversible direction sample liquid test package displacement means which operates to bi-directionally displace the thusly metered and supplied test packages through the system; a test package transfer means which operates in conjunction with the test package metering and supply means and the test package displacement means to provide for the successive test package supply and bi-directional functions of the system; test package reaction and analysis means for analysis of the thusly supplied and displaced text packages; and detection means operatively associated with the reaction and analysis means to detect and quantify the successive sample liquid test package analysis results. Such a system is particularly adapted to conduct automated clinical analysis of pluralities of human biological sample liquids and can be configured to perform various specific analyses, including well known so called chemistry and immunoassay analyses.

An embodiment of the system just described configured for conducting a chemistry analysis is shown in FIG. 1A. A second embodiment of the system just described configured for conducting an immunoassay analysis is shown in FIG. 1B.

As described in detail in the '147 and '497 patents, the system generally operates by creating a plurality of test packages and successively inserting the test packages into analytical line 30 shown in FIGS. 1A and 1B, which preferably comprises a flexible conduit made of transparent Teflon or like material. The test packages are then repeatedly and bi-directionally flowed back and forth in the analytical line 30 and ultimately past the appropriate test package reaction, analysis and detection means. Depending on the type of analysis being done, e.g., chemistry or immunoassay, particular devices are disposed along the analytical line 30 so as to comprise the reaction, analysis and detection means. As shown in FIG. 1A, a configuration appropriate for a chemistry analysis includes first, second and third flow cells 45 and vanish zone 50 disposed along the analytical line 30. The functionality of these components is described in greater detail both below and in the '147 and '497 patents. As shown in FIG. 1B, a configuration appropriate for an immunoassay analysis includes vanish zone 50, first, second and third bubble detectors 55, first and second magnets 60 and luminometer 65. The functionality of these components is described in greater detail both below and in the '147 and '497 patents.

It will be apparent to one of skill in the art that a test package suitable for a so-called sandwich type magnetic particle-based heterogeneous immunoassay is as shown in FIG. 2. In particular, this test package consists of six liquid segments: a magnetic particle suspension designated as MP, a mixture of sample and first and second reagents designated as $S/R_1/R_2$, a first wash designated as $W_1$, a second wash designated as $W_2$, a combination of a third reagent and a fourth reagent designated as $R_3/R_4$, and a marker dye designated as D. As illustrated in FIG. 2, each of these liquid segments is separated by an air segment designated as $A_1/A_3$, which is a combination of successively metered air segments $A_1$ and $A_3$, or an air segment designated as $A_2$. It will also be apparent to one of skill in the art that other suitable immunoassay test packages exist, for example a test package containing eight liquid segments.

It will also be apparent to one of skill in the art that a suitable test package for a chemistry analysis is as shown in FIG. 3. In particular, this test package consists of three liquid segments: a second reagent designated as $R_2$, a mixture of sample and a first reagent designated as $S/R_1$, and a buffer designated as B. As shown in FIG. 3, with the exception of the $S/R_1$ and $R_2$ segments, each of these liquid segments is separated by an air segment designated as $A_1$, $A_2$ and $A_3$. The $S/R_1$ and $R_2$ segments are separated by a vanish bubble VB comprising air. As described in detail in the '147 and '497 patents, this vanish bubble VB operates in connection with vanish zone 50 shown in FIG. 1A to cause a mixing of the $S/R_1$ and $R_2$ segments at an appropriate lime.

Referring again to FIGS. 1A and 1B, the sample liquid test package metering and supply means which creates the test packages described above includes an aspirating probe 10 connected to a service loop 15 which, like analytical line 30, preferably comprises a flexible conduit made of transparent Teflon or like material. Liquid supply 20 is located adjacent probe 10 and generally comprises a plurality of containers for holding and supplying the various liquids to be aspirated into the probe 10 including sample liquids, reagents, marker dyes, magnetic particle suspensions, buffers and washes.

Thus, the test packages just described are created in one or more cycles involving the alternate aspiration of segments of liquid from the liquid supply 20 and segments of air. In particular, with respect to the creation of a sandwich type immunoassay test package, during each cycle, two liquid segments, $L_1$ and $L_2$, and three air segments, $A_1$, $A_2$ and $A_3$, are alternatively aspirated into the probe 10 and up into the service loop 15 by operation of aspiration pump 25, which is selectively coupled to the service loop 15 through transfer line 35 and shear valve 40, to be described below, to create a test package component shown in FIG. 4. The order of aspiration during each cycle to create a test package component is as follows: $A_3$, $L_2$, $A_2$, $L_1$, $A_1$. Thus, a sandwich type immunoassay test package as shown in FIG. 2 is created by aspirating three successive test package components, designated as TPC-1, TPC-2 and TPC-3 in FIG. 2, in three successive cycles. In cycle 1, TPC-1 is aspirated wherein $L_2$ is the mixture of sample and first and second reagents $S/R_1/R_2$ and $L_1$ is the magnetic particle suspension MP. In cycle 2, TPC-2 is aspirated wherein $L_2$ is the second wash $W_2$ and $L_1$ is the first wash $W_1$. In cycle 3, TPC-3 is aspirated wherein $L_2$ is the marker dye D and $L_3$ is the combination of third and fourth reagents $R_3/R_4$. FIG. 5 illustrates this creation in three cycles. As shown in FIG. 5, adjacent test package components always abut one another at an $A_1/A_3$ interface. The chemistry test package, on the other hand, is simply created in one cycle by aspirating a third air segment $A_3$, then the buffer B, then a second air segment $A_2$, then the mixture of sample and first reagent $S/R_1$, then the vanish bubble VB, then the second reagent $R_2$, and finally a first segment $A_1$.

In addition, as described in the '147 and '497 patents, an isolation liquid is aspirated into the probe 10 each time a liquid is aspirated. The isolation liquid preferably comprises an appropriate fluorocarbon or similar liquid, referred to herein at times as oil, which is immiscible with the liquid supplied by liquid supply 20 and wets the hydrophobic inner walls of the system components. As a result, the system component inner walls are coated with an isolation liquid layer which substantially prevent contact therewith by the liquid and the adhesion of the same thereto.

Once the test packages are created, they are transferred to the analytical line 30 for subsequent analysis in the following manner. For an immunoassay using the system shown in FIG. 1B, the probe 10 and service loop 15 is capable of holding a maximum of two test package components. As each successive test package component making up a test package is aspirated into probe 10, the previously aspirated test package component is moved towards the shear valve 40. The service loop 15 is selectively connected to transfer line 35, also preferably comprising a flexible conduit made of transparent Teflon or like material, through shear valve 40. Thus, when the service loop 15 is full, i.e., contains two test package components, and the next successive test package component is aspirated by probe 10, the test package component contained within the service loop 15 nearest the shear valve 40 will move into the transfer line 35. The shear valve 40 is then actuated so as to align the transfer line 35 with the analytical line 30 and, by operation of the aspiration pump 25, the test package component contained within the transfer line 35 is inserted into the analytical line 30. The shear valve 40 is then actuated again so as to realign transfer line 35 with service loop 15 and the next test package component is aspirated. Thus, for each immunoassay test package shown in FIG. 2, it takes three complete actuations of shear valve 40, i.e., a complete actuation meaning from aligning the transfer loop 35 with the service loop 15 to aligning the transfer loop 35 with the analytical line 30 and back again, to move the complete immunoassay test package, one test package component at a time, into the analytical line 30. It will be appreciated by one of skill in the art that if an immunoassay test package containing eight liquid segments as described above is used, it will take four complete actuations of shear valve 40 to move the complete immunoassay test package into the analytical line 30.

For a chemistry analysis using the system shown in FIG. 1A, the transfer is virtually identical except that the probe and service loop are capable of holding two complete chemistry test packages. Accordingly, once the probe and service loop are full, as each successive test package is aspirated (in a single cycle as described above), the test package nearest the shear valve 40 moves into the transfer line 35. Thus, unlike the immunoassay system shown in FIG. 1B which requires three actuations of the shear valve 40 to move a single complete test package to the analytical line 30, in the chemistry system shown in FIG. 1A, each actuation of the shear valve 40 causes a complete chemistry test package to be inserted into the analytical line 30.

Accordingly, by operation of the probe 10, service loop 15, aspiration pump 25, transfer line 35 and shear valve 40, appropriately configured test packages are created and ultimately inserted into analytical line 30 for analysis.

Furthermore, for both systems shown in FIGS. 1A and 1B, each time the shear valve 40 is actuated to realign the transfer line 35 with the service loop 15 as described above, stream line 70 is aligned with analytical line 30 and stream pump 46 causes the stream of test packages already contained in the analytical line 30 to flow a predetermined amount or distance in the forward and reverse directions as described in detail in the '147 patents and '497 patents. This flow causes the test packages to successively move through the system and, in turn, undergo appropriate analysis.

Although the preferred embodiment of the present invention utilizes shear valve 40, any inlet valve that is capable of selectively connecting service loop 15, transfer line 35 and analytical line 30 could be used, such as a three-way valve.

As will be known by one of skill in the art, in a typical so-called sandwich immunoassay analysis, the sample S is allowed to react with first and second reagents $R_1$ and $R_2$ within the test package for a particular, fixed period of time as defined by the assay protocol. Then, the magnetic particles are transferred out of the magnetic particle suspension MP and into the $S/R_1/R_2$ segment, where they are allowed to mix for an additional specified amount of time as defined by the assay protocol. Thereafter, the magnetic particles are separated from the $S/R_1/R_2$ segment, are transferred to and washed in washes $W_1$ and $W_1$, and are transferred to and reacted with a combination of third and fourth reagents $R_3/R_4$. The reaction between the magnetic particles and the combination of third and fourth reagents $R_3/R_4$ generates a detectable response in the form of photometric signals which are in proportion to the analyte concentration in the sample S. As noted above, a suitable apparatus for carrying out such an immunoassay is shown in FIG. 1B and includes first and second magnets 60 and luminometer 65. The first magnet 60 is used to transfer the magnetic particles into the $S/R_1/R_2$ segment after a specific amount of time, and the second magnet 60 is used to transfer the magnetic particles from the $S/R_1/R_2$ segment into washes $W_1$ and $W_2$ and ultimately into the $R_3/R_4$ segment. The luminometer 65 is used to detect and measure the photons emitted from the segment $R_3/R_4$ containing the magnetic particles.

Another well known type of immunoassay is the so-called competitive immunoassay. In the test package for a competitive immunoassay, a mixture of sample and a first reagent $S/R_1$ are separated from a second reagent $R_2$ by a vanish bubble VB. Thus, the sample S and first reagent $R_1$ are preincubated in the analytical line 30 for a fixed period of time before being mixed with the second reagent $R_2$ through operation of the vanish zone 50. Then, the remainder of the method proceeds as described above in connection with the sandwich method.

As will be known by one of skill in the art, in a typical chemistry analysis a mixture of the sample and a first reagent $S/R_1$ are separated from a second reagent $R_2$ by a vanish bubble VB. Thus, the sample S and first reagent $R_1$ are pre-incubated in the analytical line 30 for a fixed period of time before being mixed with the second reagent $R_2$ through operation of the vanish zone 50. The chemical reaction between the sample S, reagent $R_1$ and reagent $R_2$ produces a chromofore which absorbs light at a specific wavelength. The light absorption is measured every time a $S/R_1/R_2$ segment passes through the Flow Cells 45. Since the light absorption is proportional with the concentration of chromofore, which in turn depends on the amount of the analyte in the sample, the analyte concentration can be determined.

In the systems just described, it is very important to keep the timing of the various analyses, whether it be the chemistry or the immunoassay, very accurate and uniform. In particular, in the chemistry method it is important that all test packages pass the vanish zone and the flow cells at precise and uniform times, and in the immunoassay method it is important that all test packages reach the first magnet and the second magnet (where the magnetic particles are removed from the $S/R_1/R_2$ segment, thereby terminating the immunochemical reactions) at very precise and uniform times. In order to achieve and maintain such precise timing, it is necessary for the test packages to be maintained at a uniform and consistent length.

The uniformity among test packages can be adversely effected during the aspiration thereof in the following manner. When a liquid with a high surface tension, such as serum, is aspirated, the thickness of the isolation liquid film in the probe 10 and service loop 15 decreases and a portion of the isolation liquid is displaced and pushed ahead of the segment with the high surface tension. The displacement of oil results in a change in the volume of the probe 10 and service loop 15. As a result, shearing would not occur in the middle of the $A_1/A_3$ segment, which normally causes the insertion of small air segments into the analytical line 30, which can result in a substantial decrease in the length of the stream.

In addition, in connection with an immunoassay, it is extremely important for the glowing segment, i.e., the $R_3/R_4$ segment mixed with the magnetic particles that is emitting photons, to have a constant velocity as it passes through the luminometer 65. If the velocity is not constant, the dwell time, meaning the length of time the glowing segment spends in the luminometer read head, will vary, and the number of photons counted will be incorrect. For example, if the speed of the stream is lower than it should be, the dwell time will be higher, and more photons will be counted. As a result, the measured light intensity will be overestimated and the results will be distorted.

Moreover, in connection with a chemistry analysis, it is generally desirable to take measurements on a specific predetermined number of test packages at the first flow cell 45 during the forward flow of the stream of test packages in the analytical line 30. If the length of the test packages, and thus the stream, becomes too large, less test packages will be observed during the forward flow of the stream for a given movement of the stream pump 46. If the length of the test packages becomes too small, more test packages will be observed during the forward flow of the stream and there is a higher probability for undesirable merging of adjacent liquid segments inside the vanish zone 50. In addition, if the length of the stream is permitted to vary, the timing at which the test packages reach the flow cells 45 will be thrown off. It is important that the timing be accurate because the accuracy of the measurements to be taken depends on the state of the reactions taking place in the test packages, which in turn depends on the reaction rate.

SUMMARY OF THE INVENTION

The present invention relates to a method and apparatus for controlling a stream of liquid and air segments wherein the liquid and air segments are selectively aspirated into a first fluid conduit in a plurality of cycles, each cycle beginning with the aspiration of a first air segment and ending with the aspiration of a final air segment. The first and final air segments each have a volume. The liquid and air segments are then transferred from the first fluid conduit to a second fluid conduit. The volume of the final air segment of each cycle is adjusted after the final air segment has moved into the second fluid conduit. Next, the liquid segments and the air segments of each cycle are transferred from the second fluid conduit to a third fluid conduit. The volume of the first air segment of each cycle is then adjusted after the first air segment has moved into the third fluid conduit.

One aspect of the present invention is directed to an apparatus for controlling a stream of liquid packages, each liquid package comprising a plurality of liquid and air segments. The apparatus includes a probe for selectively aspirating liquid segments and air segments into a first fluid conduit in a plurality of cycles wherein each cycle ends with the aspiration of a final liquid segment and a final air segment in that order. The apparatus further includes a second fluid conduit and a valve coupled to the first fluid conduit and the second fluid conduit. The valve is adapted to be actuated between a first position in which the second fluid conduit is coupled to the first fluid conduit and a second position in which the second fluid conduit is not coupled to the first fluid conduit. An air and liquid interface detector is positioned along the second fluid conduit a fixed distance from the valve, the fixed distance corresponding to a predetermined fixed volume within the second fluid conduit. The apparatus includes means for stopping the aspiration of the final air segment in a current cycle when the air and liquid interface detector detects an interface between an air segment and a liquid segment of a previous cycle which have moved into the second fluid conduit after the final liquid segment of the previous cycle has fully entered the second fluid conduit and for actuating the valve from the first position to the second position at a time subsequent to this detection.

A further aspect of the present invention is directed to a method for controlling a stream of liquid packages wherein each liquid package comprises a plurality of liquid and air segments. The method includes selectively aspirating liquid segments and air segments into a first fluid conduit in a plurality of cycles, each cycle ending with the aspiration of a final liquid segment and a final air segment in that order. The first fluid conduit is coupled to a valve and the valve is coupled to a second fluid conduit. The valve is adapted to be actuated between a first position in which the first fluid conduit is coupled to the second fluid conduit and a second position in which the first fluid conduit is not coupled to the second fluid conduit. The method further includes detecting an interface between an air segment and a liquid segment of a previous cycle which have moved into the second fluid conduit at a position along the second fluid conduit which is a fixed distance from the valve after the final liquid segment of the previous cycle has fully entered the second fluid conduit. The fixed distance corresponds to a predetermined fixed volume within the second fluid conduit. The method also includes stopping the aspiration of the final air segment in a current cycle when the interface has been detected and actuating the valve from the first position to the second position at a time subsequent to this detection.

A further aspect of the present invention is directed to an apparatus for controlling a stream of liquid packages wherein each liquid package comprises a plurality of liquid and air segments. The liquid packages are formed in one or more cycles of aspiration of liquid and air segments, each cycle beginning with the aspiration of a first air segment and a first liquid segment. The apparatus includes a fluid conduit into which the liquid and air segments aspirated in each of the cycles are inserted and in which the stream of liquid packages is repeatedly bi-directionally flowed in a forward and reverse direction. The apparatus further includes a valve coupled to a first end of the fluid conduit and an air and liquid interface detector positioned along the fluid conduit adjacent the valve. Also provided are means for stopping the flow of the stream of liquid packages in the reverse direction at a point in time when the air and liquid interface detector detects an interface between the first air segment and the first liquid segment most recently inserted into the fluid conduit adjusted by a delay, wherein the delay is normalized around a predetermined nominal center point delay according to a feedback loop.

A still further aspect of the present invention relates to a method for controlling a stream of liquid packages, each liquid package comprising a plurality of liquid and air segments. The method includes selectively aspirating liquid segments and air segments in a plurality of cycles, each cycle beginning with a first air segment and a first liquid segment, and inserting the liquid segments and the air segments aspirated in each of the cycles into a fluid conduit having a first end such that for each of the cycles the first liquid segment and the first air segment are the next-to-last and the last liquid and air segment, respectively, inserted. The method further includes flowing the stream of liquid packages in a forward direction and a reverse direction in the fluid conduit and detecting an interface between the first air segment and the first liquid segment most recently inserted into the fluid conduit at a reference location along the fluid conduit adjacent the first end of the fluid conduit when the stream is flowing in the reverse direction. The flow of the stream is stopped at a point in time when the interface is detected adjusted by a delay, the delay being normalized around a predetermined nominal center point delay according to a feedback loop.

According to still a further aspect of the present invention, the feedback loop described above is based upon a time difference TD equal to $T_2-T_1$, wherein $T_1$ is a time at which a first particular liquid segment of a particular liquid package reaches a reference point during the flow of the stream in the forward direction and $T_2$ is a time at which a second particular liquid segment of the particular liquid package reaches a reference point during the flow of the stream in the reverse direction. In an aspect of the invention, the delay is calculated according to the following formula:

Delay=$CP$-Error*$K$, wherein CP is the predetermined nominal center point delay, Error is equal to a predetermined set point minus TD, and K is a gain factor.

According to still a further aspect of the present invention, the feedback loop is based upon a difference between a target liquid package length and an average length, wherein the liquid and air segments aspirated in each of the cycles and inserted into the fluid conduit each comprise a liquid package having a length, wherein the length is measured for a plurality of the packages during the flow of the stream in either the forward or reverse direction and wherein an average length is calculated using a plurality of the measured lengths. In an aspect of the present invention, the delay is calculated according to the following formula:

Delay=$CP$-Error*$K$, wherein CP is the predetermined nominal center point delay, Error is equal to the target liquid package length minus the average length, and K is a gain factor.

BRIEF DESCRIPTION OF THE DRAWINGS

Further features and advantages of the invention will be apparent upon consideration of the following detailed description of the present invention, taken in conjunction with the following drawings, in which like reference characters refer to like parts, and in which.

DETAILED DESCRIPTION

Figure 6A:
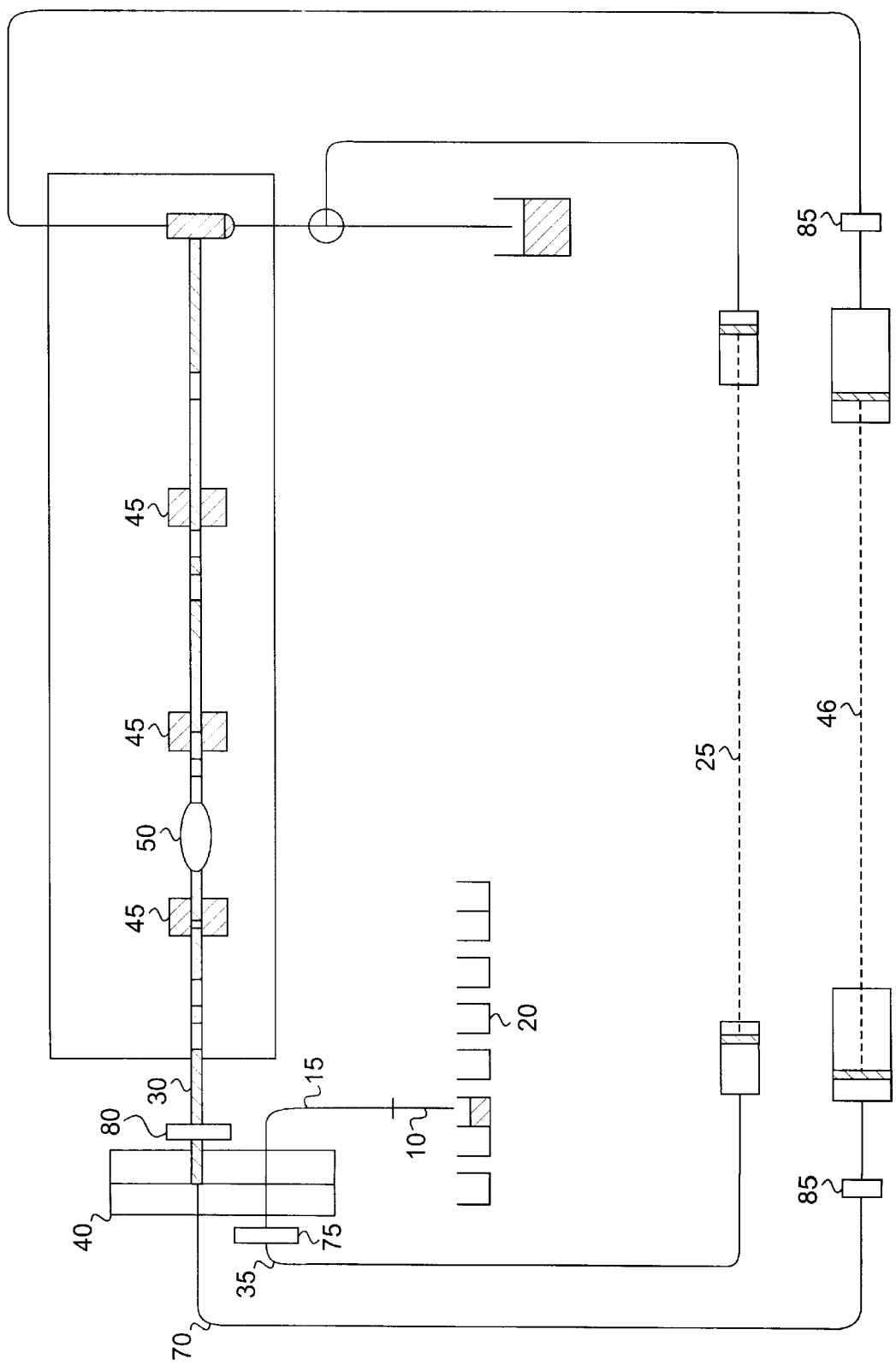
FIG. 6A is a diagram of a capsule chemistry sample liquid analysis system according to an aspect of the present invention configured for conducting a chemistry analysis.
Figure 6B:
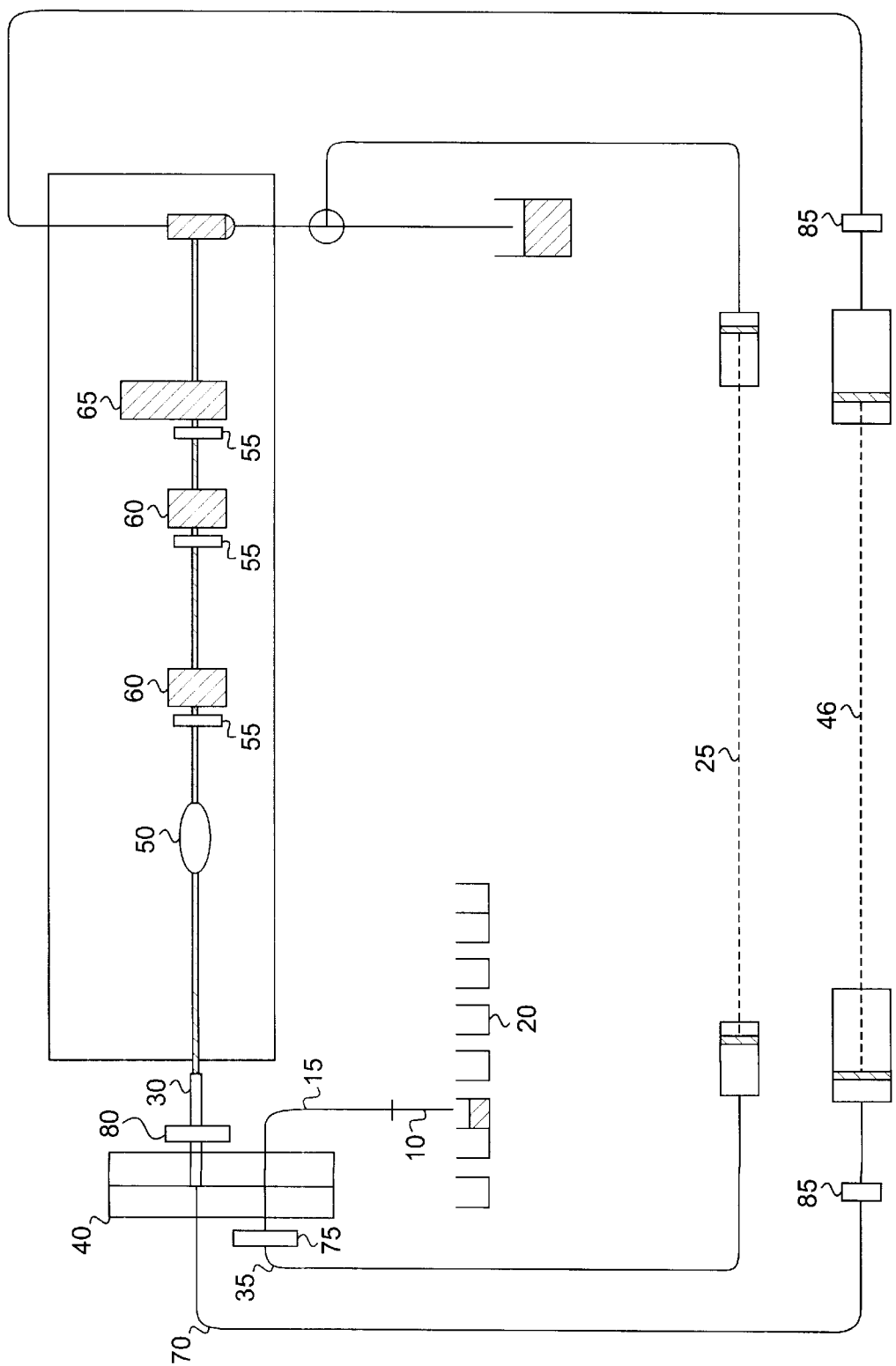
FIG. 6B is a diagram of a capsule chemistry sample liquid analysis system according to an aspect of the present invention configured for conducting an immunoassay analysis.

Referring to FIGS. 6A and 6B, embodiments of the system according to an aspect of the present invention configured for conducting a chemistry analysis and an immunoassay analysis, respectively, are shown. As shown in FIGS. 6A and 6B, transfer line bubble detector 75 is affixed along transfer line 35. Bubble detectors are well known in the art and are capable of sensing an interface between an air segment and a liquid segment in a flowing stream of air and liquid segments. Examples of suitable bubble detectors are described in U.S. Pat. No. 5,466,946 and U.S. application Ser. No. 08/995,738, both owned by the assignee hereof, the disclosures of which are incorporated herein by reference. As an alternative to a bubble detector, other devices capable of detecting an interface between an air segment and a liquid segment could be used without departing from the scope of the present invention. For example, a conductivity sensor which detects the conductivity within a fluid conduit when a liquid is present therein could be used.

Figure 1A:
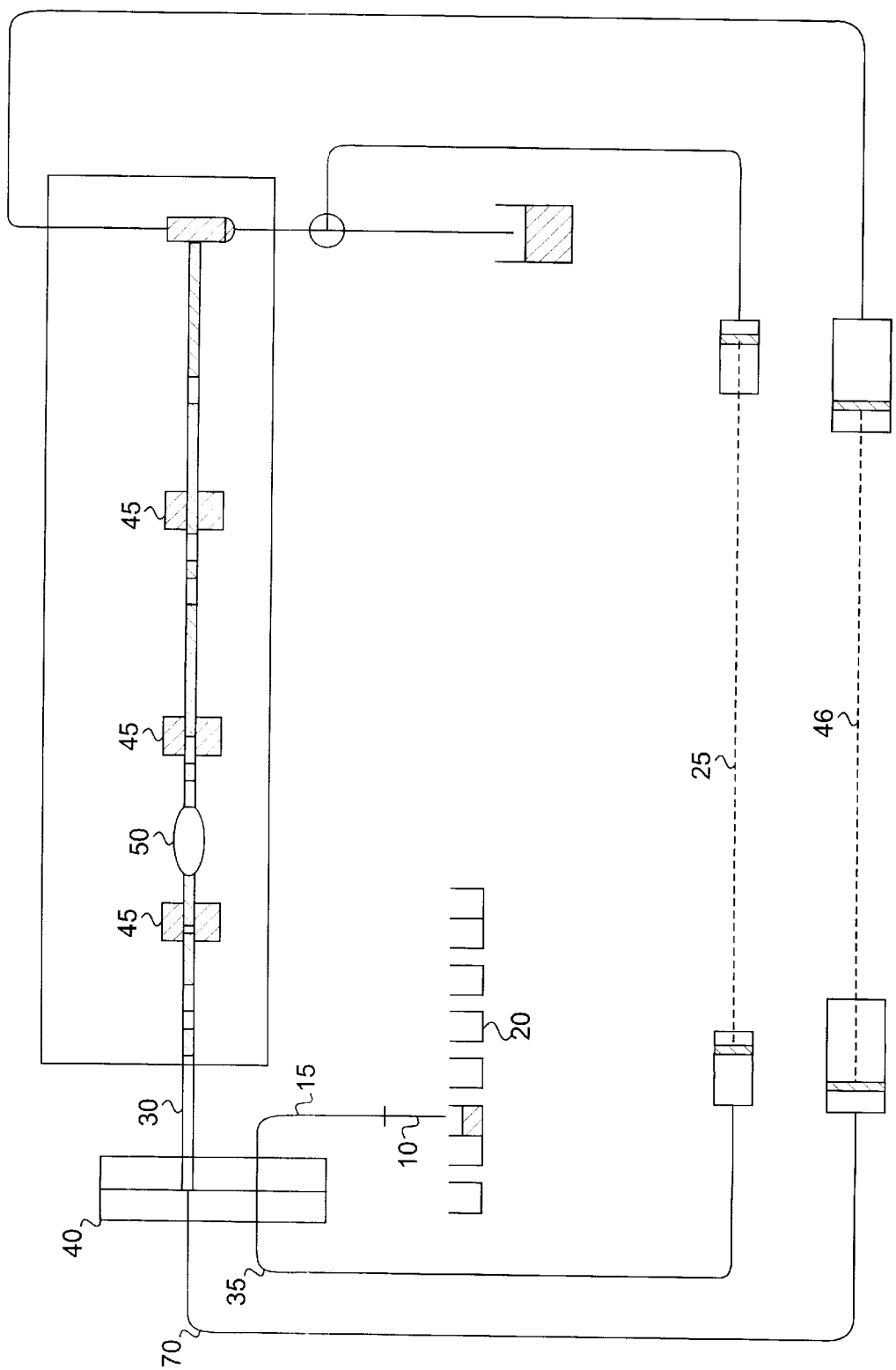
FIG. 1A is a diagram of a prior art capsule chemistry sample liquid analysis system configured for conducting a chemistry analysis.
Figure 1B:
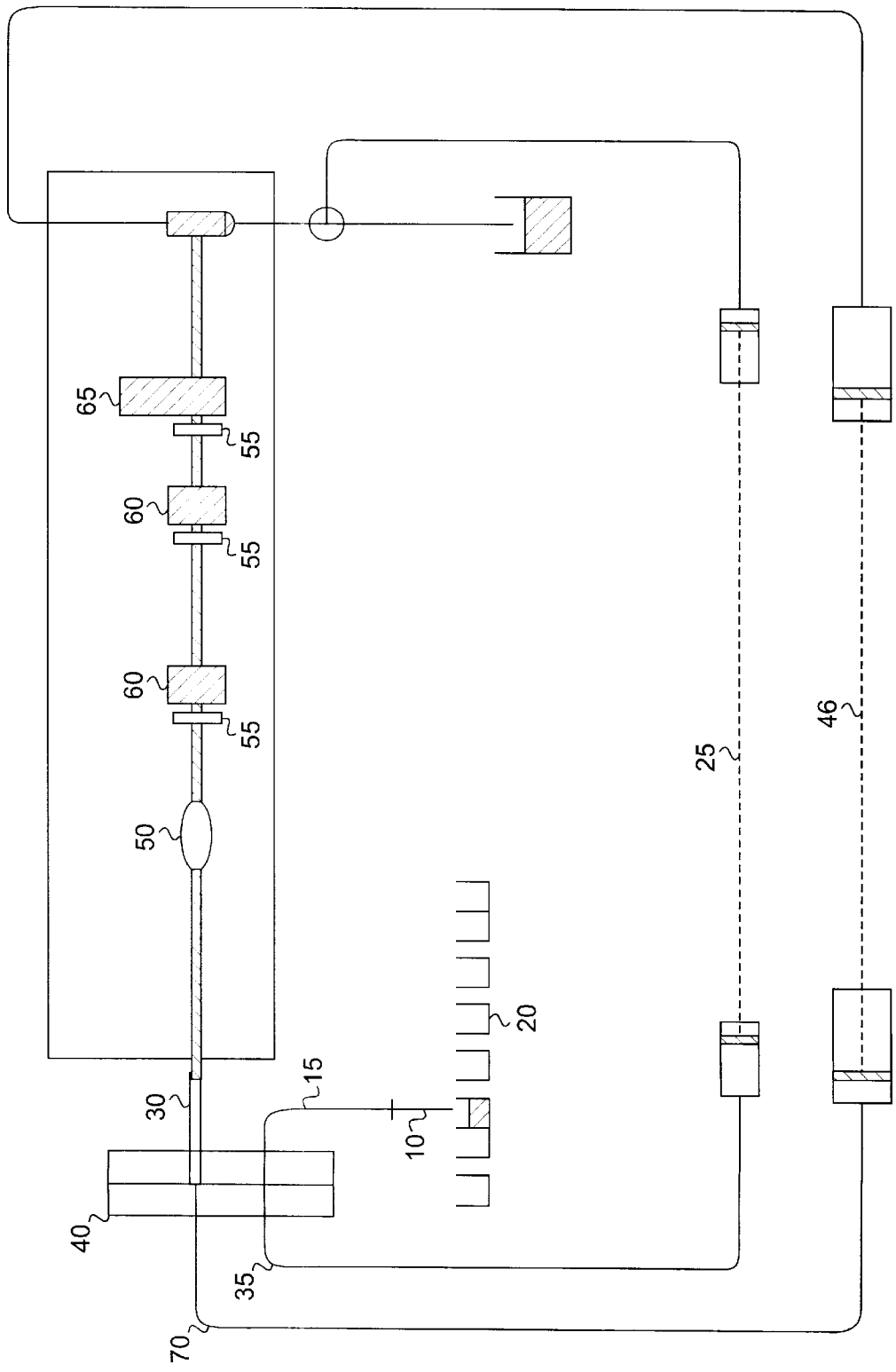
FIG. 1B is a diagram of a prior art capsule chemistry sample liquid analysis system configured for conducting an immunoassay analysis.
Figure 2:
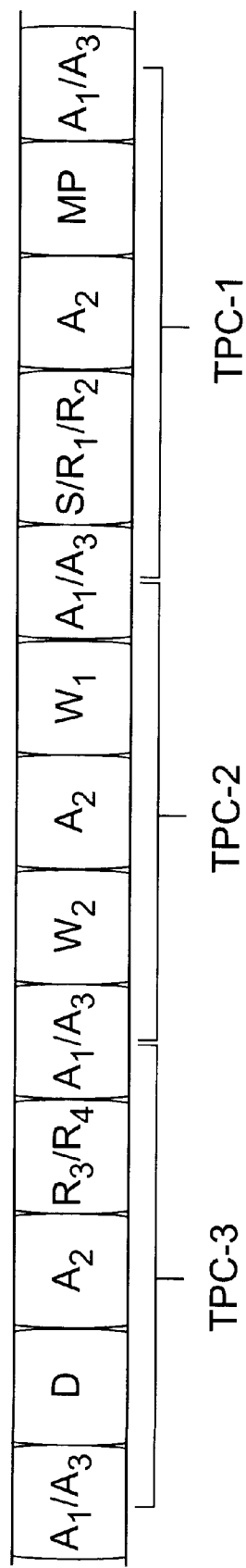
FIG. 2 is a diagram of a liquid test package suitable for conducting a magnetic particle-based heterogeneous immunoassay analysis.
Figure 3:
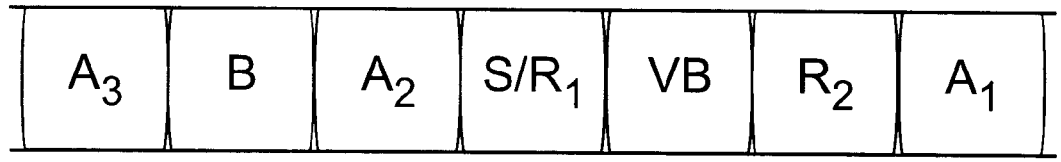
FIG. 3 is a diagram of a liquid test package suitable for conducting a chemistry analysis.
Figure 4:
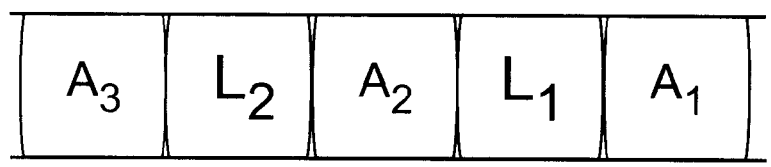
FIG. 4 is a diagram of a liquid test package component comprising a portion of the liquid test package shown FIG. 2.
Figure 5:
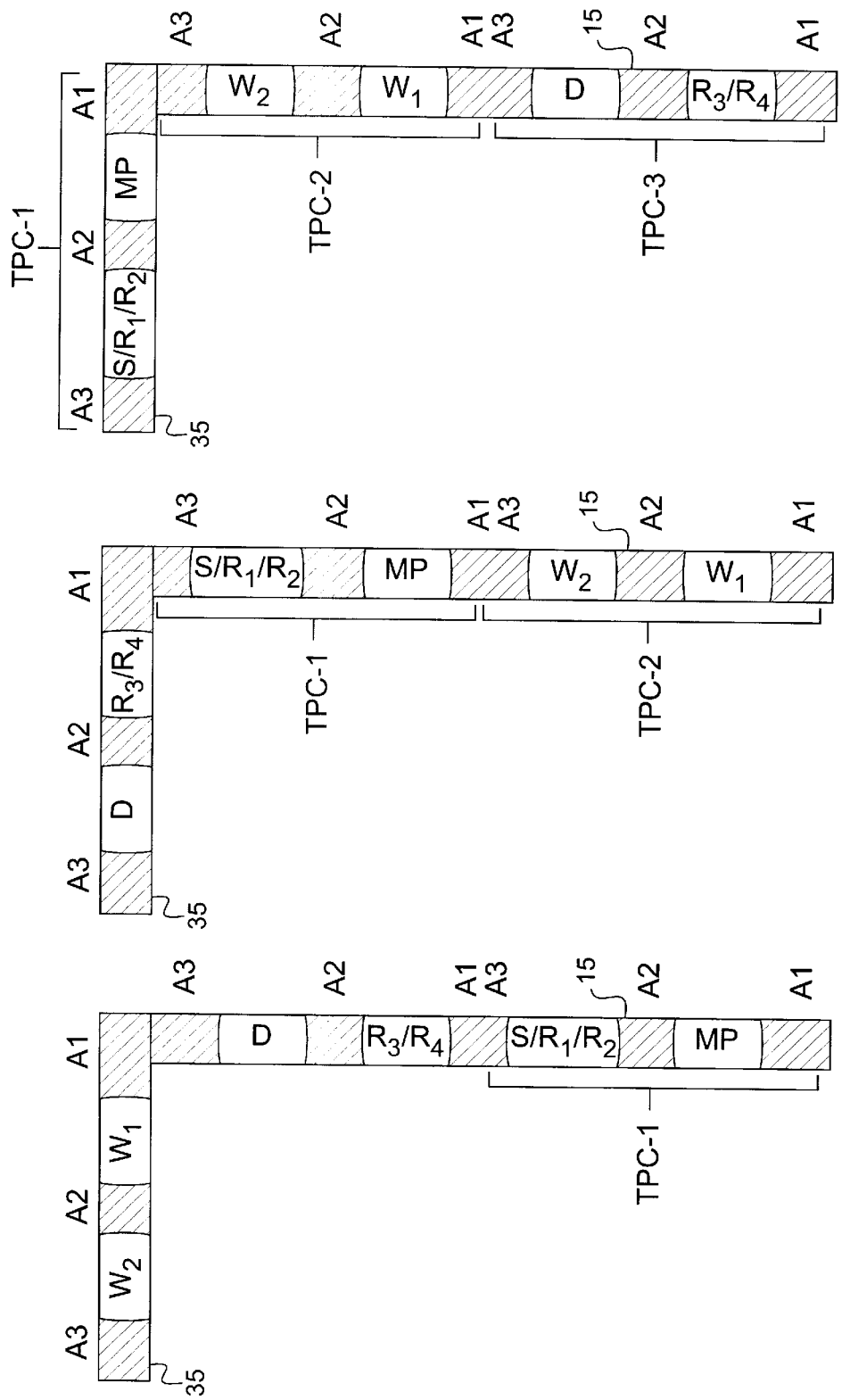
FIG. 5 is a diagram showing the service loop and transfer line of the system shown in FIG. 1B which illustrates the creation of the liquid test package shown in FIG. 2 in three cycles.
Figure 7:
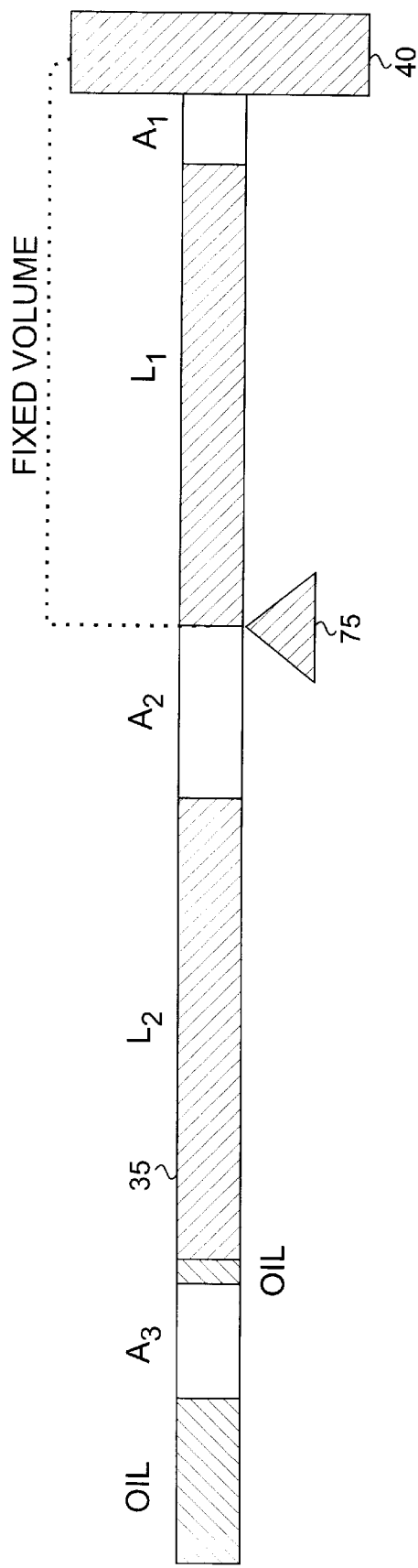
FIG. 7 is a diagram showing the transfer line, shear valve and transfer line bubble detector of the system shown in FIG. 6B according to an aspect of the present invention.

FIG. 7 is a diagram showing transfer line 35, shear valve 40 and transfer line bubble detector 75 of FIGS. 6A and 6B. For illustrative purposes, the function of the transfer line bubble detector 75 will be described in connection with a sandwich type immunoassay analysis. Thus, in FIG. 7, transfer line 35 has inserted therein a test package component as described above in connection with FIG. 4 comprising $A_3$, $L_2$, $A_2$, $L_1$ and $A_1$. It should be understood, however, that the configuration and operation described herein is not to be limited to systems performing only immunoassay analyses, but rather would apply equally to systems performing other analyses such as the chemistry analysis described above. As will become apparent below, the only limitation to the application of the transfer line bubble detector concept to be described herein is that it would not be applicable to test package components in which the sample is in the first test package component adjacent to the shear valve 40 in FIG. 7, such as a serology method.

As shown in FIG. 7, according to an embodiment of the present invention, the transfer line bubble detector 75 is positioned a fixed distance from the shear valve 40 equivalent to the combined volume of $L_1$ and $A_1$ of the test package component. In appropriate circumstances, the positioning of the transfer line bubble detector 75 may be adjusted for a system delay in stopping the aspiration pump 25. The fixed distance corresponds to a fixed volume within the transfer line 35 equal to the sum of the preferred volumes of the $L_1$ and $A_1$ segments. According to a preferred embodiment of the present invention, in the test package components which make up the sandwich type immunoassay test package, the volume of $A_2$ is between 15 and 20 $\mu l$ due to the tolerance on the volume of the aspiration syringe of probe 10, and most preferably 14 $\mu l$, the volumes of $A_1$ and $A_3$ are 7 $\mu l$ each, and the volumes of $L_1$ and $L_2$ are 28 $\mu l$ each. Thus, in this preferred embodiment, the sum of $A_1$ and $A_3$ is always 14 $\mu l$.

As noted above, it is important to keep the volumes of the $A_1$ and $A_3$ of each test package component constant, preferably 7 $\mu l$, because it is important to keep the volume, and consequently the length, of each test package component and thus the length of each test package uniform in order to maintain accurate timing as the stream of test packages moves through the system. In the preferred embodiment of the present invention for conducting an immunoassay analysis, the first magnet 60 in analytical line 30 must transfer the magnetic particles from the magnetic particle suspension MP into $S/R_1/R_2$ segment 13 minutes after insertion into the analytical line 30 and the second magnet 60 in analytical line 30 must transfer the magnetic particles out of the $S/R_1/R_2$ segment at 19 minutes after inserting into the analytical line 30. However, as discussed above, the length of the test package components can be adversely affected when a liquid with a high surface tension is aspirated into probe 10. This adverse effect may throw off this critical timing.

Figure 8:
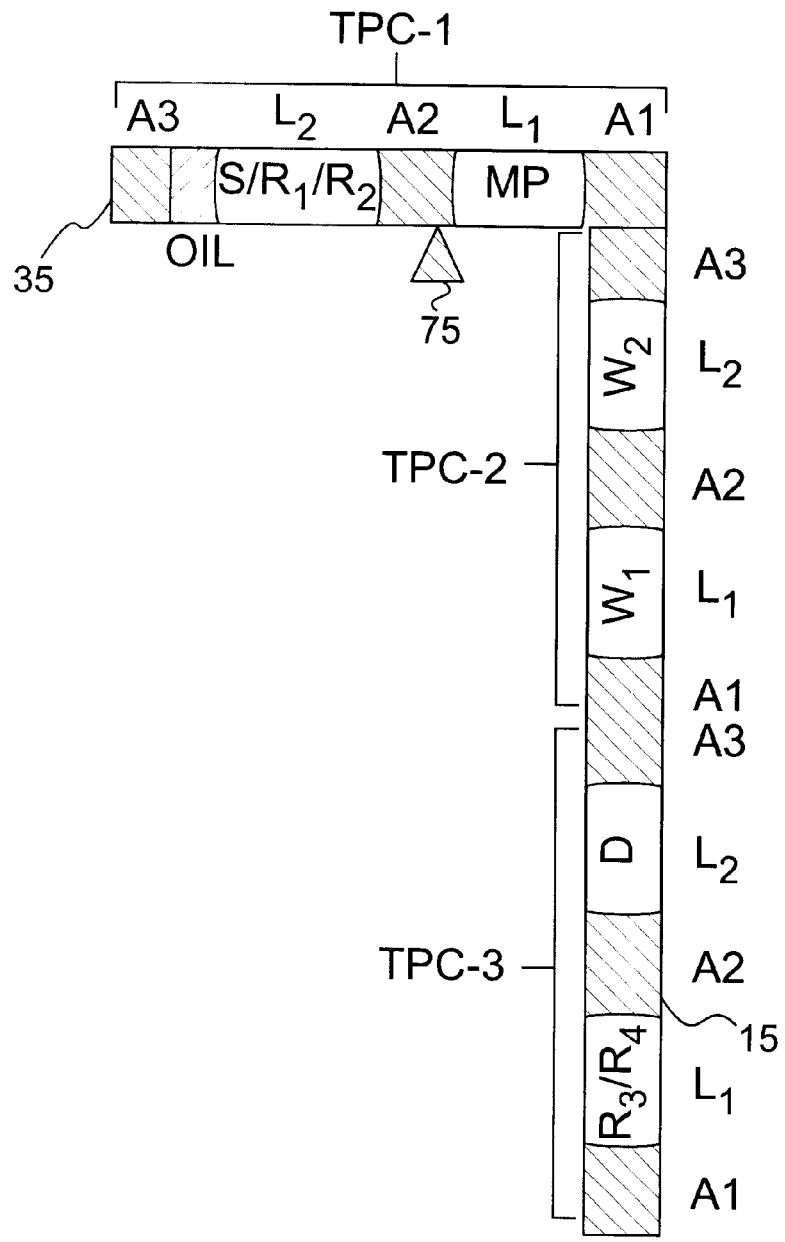
FIG. 8 is a diagram showing the probe, service loop, transfer line, shear valve and transfer line bubble detector of the system shown in FIG. 6B according to an aspect of the present invention which illustrates the creation of the liquid test package shown in FIG. 2.

Thus, referring to FIGS. 7 and 8, this problem is solved according to an aspect of the present invention by controlling or altering the volume of the Al segment of the test package component that is located in the transfer line 35 and that is about to be inserted into the analytical line 30 (TPC-1 in FIG. 8). Specifically, as noted above, adjacent test package components always abut one another at an $A_1/A_3$ interface. The volume of the $A_1$ segment in the transfer line 35 is controlled or altered by controlling the point at which the $A_1/A_3$ interface is sheared by the shear valve 40 as the test package component is moved into the transfer line 35. According to an aspect of the present invention, the $A_1/A_3$ interface is sheared based on the transfer line bubble detector 75 detecting the interface between the $A_2$ and $L_1$ segments of the test package component as that test package component is moved into the transfer line 35 from the service loop 15. When this interface is detected, the aspiration pump 25 stops aspirating the current segment of the current test package component being created (TPC-3 in FIG. 8), which, as will be apparent, and as is shown in FIG. 8, will be the $A_1$ segment of that test package component. Then, at some subsequent time, the shear valve 40 is actuated to align the transfer line 35 with the analytical line 30. This operation, i.e., stopping aspiration, may cause the $A_1$ segment of the current segment pair, meaning adjacent liquid and air segments, being created to be smaller or larger than the preferred value. Thus, in order to compensate, the $A_3$ segment aspirated in the next cycle will be aspirated to a volume equal to 14 $\mu l$ minus the volume of $A_1$, thereby resulting in a total $A_1$ and $A_3$ volume equal to the preferred volume of 14 $\mu l$. The above-described operation of transfer-line bubble detector 75 results in test packages in which the $A_1$ and $A_3$ air segments are of a uniform specific volume. Also, $A_2$, $L_2$ and $L_1$ are of uniform specific volumes and are accurately metered by the aspiration pump 25.

Alternatively, the transfer line bubble detector 75 could be positioned along the transfer line 35 such that the fixed distance corresponds to a fixed volume equal to the preferred volume of the $A_1$ segment. Thus, in this configuration, the $A_1/A_3$ interface will be sheared based on the detection of the interface between the $L_1$ and $A_1$ segments in the transfer line 35. Other variations of the placement of the transfer line bubble detector and thus variations on the above-described fixed volume are possible and will be apparent to one of skill in the art. Regardless of the placement of the transfer line bubble detector 75, it always detects an appropriate liquid and air interface after the $L_1$ segment has been fully inserted into the transfer line 35.

All of the necessary control described above is provided by appropriate software, the details and specific implementations of which would be readily apparent to one of skill in the art and thus will not be described herein. The software is stored on a hard disk and is loaded into a data acquisition computer at startup.

Furthermore, as noted above, in the case of an immunoassay analysis, it is important for the glowing segment, i.e. the $R_3/R_4$ liquid segment containing magnetic particles that is emitting photons, to have a constant velocity as it passes through the luminometer 65 placed along analytical line 30. A constant velocity can be achieved by maintaining a fixed distance between the position of the glowing segment and the luminometer 65 at the start of the forward stream motion during which glowing segment moves past the luminometer 65. The range of variation of the position of the glowing segment at the start of the forward stream should be no more than ±1 segment. To achieve a positional stability of ±1 segment, the entire length of the air and liquid segments in the analytical line 30 from the shear valve 40 to the second magnet 60 must not vary by more than ±0.5%.

In order to provide this stability and thus maintain the constant velocity described above, as shown in FIG. 6B, the system according to an aspect of the present invention includes shear valve bubble detector 80 placed along analytical line 30 adjacent to shear valve 40 which operates in conjunction with a feedback loop to be described below.

Preferably, the shear valve bubble detector 80 is positioned at a distance corresponding to at least 7 µl to the shear surface of the shear valve 40. The excess volume above 7 microliters is used to allow for the distance needed by the stream to stop. As noted above, other devices capable of detecting an interface between a liquid segment and an air segment could be used as an alternative to shear valve bubble detector 80.

As described above, the test package components forming immunoassay test packages are inserted into analytical line 30 by operation of transfer line 35, shear valve 40 and aspiration pump 25 such that the last segment to enter analytical 30 is always the $A_3$ segment. Also as described above and in detail in the '147 and '497 patents, after each successive test package component is inserted into analytical line 30, the shear valve 40 is actuated to align stream line 70 with analytical line 30, and by operation of stream pump 46, the stream in the analytical line 30 is flowed a predetermined amount in first the forward and then the reverse direction.

Figure 9:
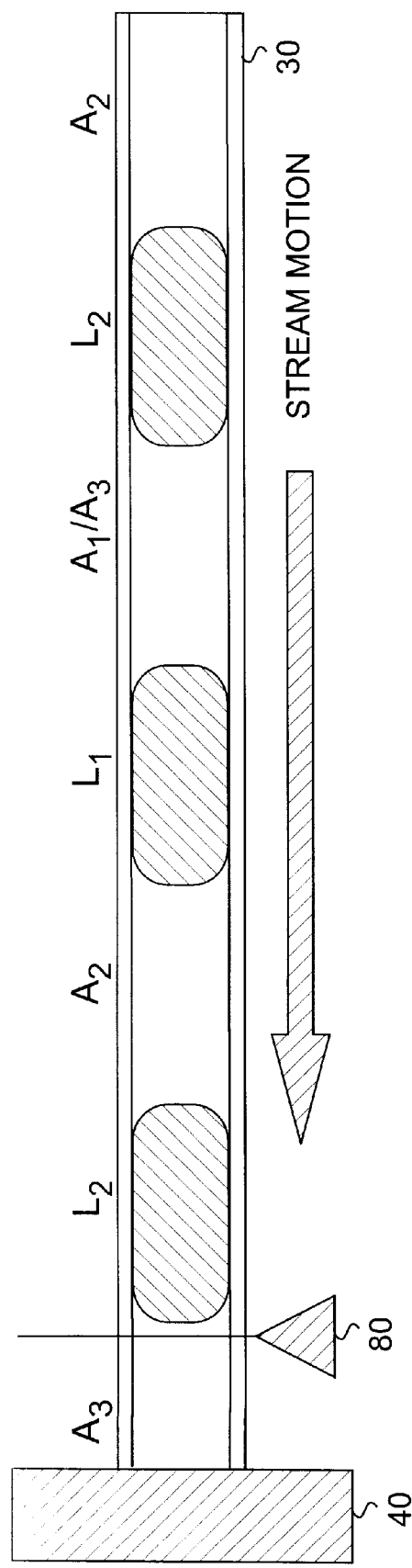
FIG. 9 is a diagram showing the analytical line, shear valve and shear valve bubble detector of the system in FIG. 6B according to an aspect of the present invention.

In order to monitor and control the length of the stream in analytical line 30 and thus maintain the necessary fixed distance between each glowing segment of each test package and the luminometer 65, the size of the $A_3$ segment of each new test package component inserted into the analytical line 30 is controlled, i.e., increased or decreased. This control and manipulation is accomplished by the shear valve bubble detector 80, the shear valve 40, and stream vent valves 85 which, when activated, stop the flow of the stream in analytical line 30. In particular, referring to FIG. 9, as the stream is flowed in the direction toward the shear valve 40, i.e., the reverse direction, the $A_3/L_2$ interface is detected by the shear valve bubble detector 80 and, after a programmed delay of up to 300 milliseconds after this detection, the stream line vent valves 85 are activated to stop the stream. The particular programmed delay is determined by a feedback control loop to be described below. After the stream line vent valves 85 are activated, the shear valve 40 is actuated, thereby altering the size of the $A_3$ segment. The resized $A_3$ segment is combined with the $A_1$ segment of the next inserted test package component from the transfer line 35 to yield an air segment $A_1/A_3$ of a controlled volume. Thus, the size of the air segments formed at the shear valve 40 depend on the delay between the time that the shear valve bubble detector 80 senses the $A_3/L_2$ interface of the last test package component in the returning stream, and the time that the stream vent valves 85 are activated to stop the stream.

Figure 10:
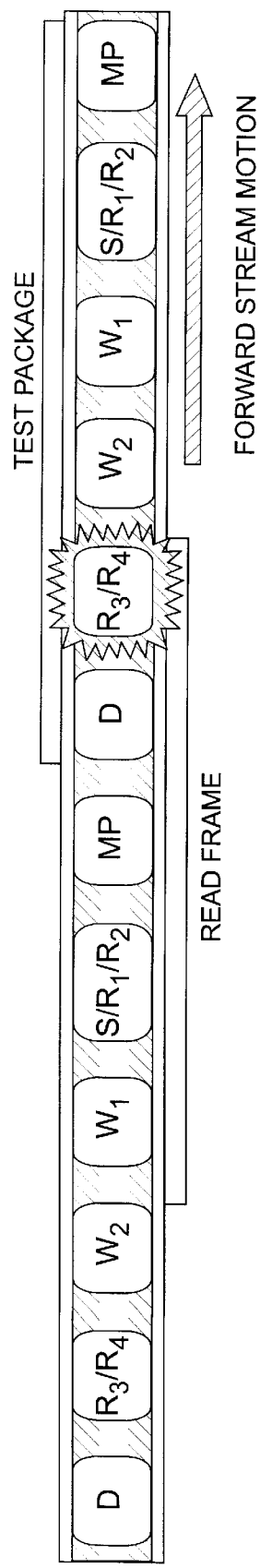
FIG. 10 is a diagram showing the analytical line of the system shown in FIG. 6B which illustrates a read frame according to an aspect of the present invention.

The feedback control loop which determines the appropriate delay described above will now be described with reference to FIGS. 10 through 12. The feedback control loop uses as its basis for measurement what is known as a read frame comprising particular portions of adjacent test packages. In particular, as shown in FIG. 10, each read frame starts at the air-liquid interface of the $R_3/R_4$ segment of one test package, and ends at the air-liquid interface of the $W_2$ segment from the next successive test package.

Figure 11:
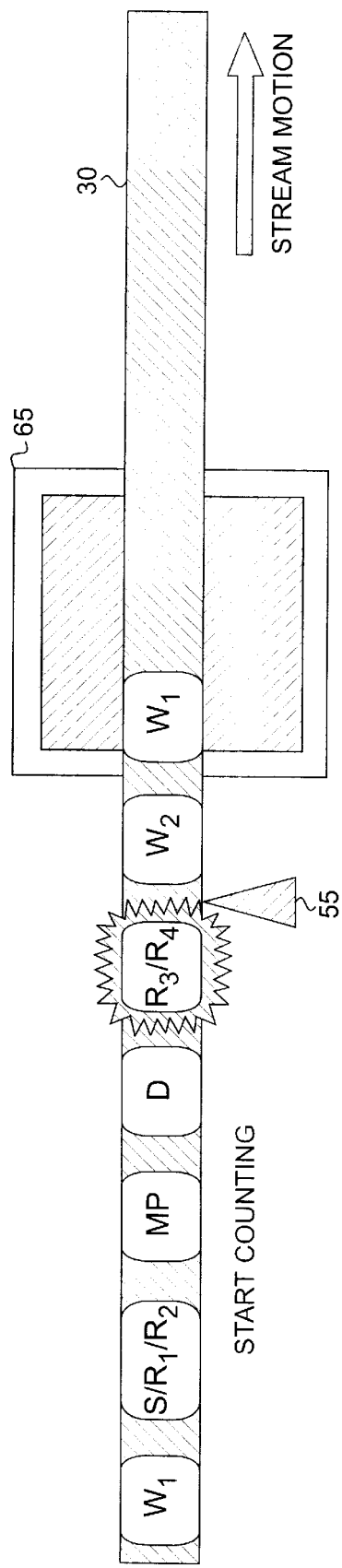
FIGS. 11 and 12 are diagrams of the analytical line and luminometer of the system shown in FIG. 6B which illustrates the times at which the luminometer starts and stops counting photons.
Figure 12:
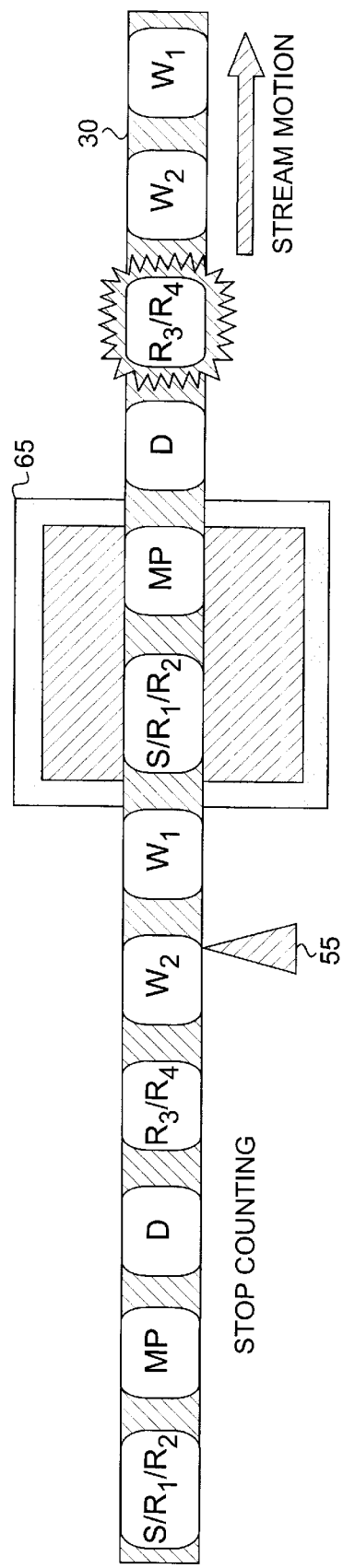

As shown in FIG. 11, when the beginning of the read frame reaches the bubble detector 55 closest to luminometer 65 in FIG. 6B during the forward flow of the stream, the luminometer 65 begins counting photons and the time is recorded. As shown in FIG. 12, when the end of the read frame reaches the bubble detector 55 during the forward flow of the stream, the luminometer 65 stops counting photons and the data is saved. After the five liquid segments comprising the read frame have passed through the luminometer in the forward direction (left to right in FIGS. 11 and 12), the stream flow stops and reverses direction. When the end of the read frame reaches bubble detector 55 during the reverse flow of the stream, the luminometer 65 starts counting photons again and the time, $T_2$, is recorded. When the front of the read frame reaches bubble detector 55 during the reverse flow of the stream, the luminometer 65 stops counting photons and the data is saved.

As noted above, the goal is to have the read frame, in particular the glowing segment, start far enough back from the luminometer 65 in both the forward and reverse directions such that the stream has time to reach a constant velocity during the time in which photons are counted. This goal is accomplished according to an aspect of the present invention by controlling the stream start position in such a way that the time differential TD, equal to $T_2$ minus $T_1$, remains close to a predetermined set point. In a preferred embodiment of the present invention, the set point is equal to 3700 milliseconds. If the stream starts forward at too great a distance from the luminometer 65 and bubble detector 55, TD will be too small. To remedy this problem, more air will need to be added to the front end of the stream (at the shear valve 40) to push the stream front closer to the luminometer 65. This is done by decreasing the shear valve bubble detector delay described above. Similarly, if the stream starts forward at too little a distance from the luminometer 65, TD will be too large. To remedy this problem, the stream front will need to be moved away from the luminometer 65 by decreasing the air at the front end of the stream using an increased shear valve bubble detector delay.

The appropriate control is accomplished by means of a proportional integral differential control loop where only the proportional element of control is used. In such a control loop according to an aspect of the present invention, the shear valve bubble detector delay is calculated according to the following equation:

$$\text{Delay}=CP-\text{Error}*K,$$

wherein CP is the nominal value of the delay which results in air segments of nominal or normal size, which will vary depending on the particulars of the analytical line 30, Error equals the set point, described above, minus TD, and K is a gain factor. In a preferred embodiment of the present invention, the nominal value of the delay CP is equal to 200 milliseconds, which results in air segments of about 17 µl, and K is equal to 0.5. Furthermore, the value of Error is limited to from −200 to +200 milliseconds. Error values outside of this range are not expected and are eliminated in order to prevent excessive delay adjustments. Thus, as will be apparent, the shear value bubble detector delay is normalized to ±100 milliseconds around the control range center point CP.

In addition, as noted above, in the case of a chemistry analysis, the goal is to take measurements on a specific predetermined number of test packages, preferably 13, at the first flow cell 45 during each forward flow of the stream of test packages in the analytical line 30. In order to achieve this goal, which depends on controlling the length of the test packages and thus the length of the stream, a feedback loop, similar to the one described above in connection with an immunoassay analysis, which operates in conjunction with shear valve bubble detector 80 is used. In particular, this feedback control loop controls the delay between the time at which the shear valve bubble detector 80 detects the interface between the $A_3$ and B segments of the last test package in the returning stream and the time at which the stream vent valves 85 are activated to stop the stream. Thus, the size of each new $A_3$ segment inserted into the analytical line 30 can be controlled.

In the chemistry feedback loop, instead of measuring TD equal to $T_2$ minus $T_1$, the length of a set of test packages, measured from buffer B to buffer B, is measured during the forward or reverse motion of the stream in the analytical line 30. The length of each test package is actually measured in terms of the transit time of the test package past one of the flow cells 45, preferably the first flow cell 45. Facilitating this function is the fact that each flow cell 45 is provided with the capability to detect liquid to air interfaces much like a bubble detector. Thus, the set of test packages whose lengths are measured comprises all of those test packages that pass the particular flow cell 45 during either the forward or reverse motion of the stream, whichever the case may be. An average test package length, Taver, is then calculated using the measured lengths. In a preferred embodiment, only the measured lengths of certain of the test packages that satisfy certain criteria to be described below are used to calculate Taver. This average is then compared to a target test package length, Tset. With an average test package length equal to Tset, the correct number of test packages will be measured by the first flow cell 45. If the average test package length is too large, it is necessary to reduce the size of the $A_3$ segment of the last test package inserted into the analytical line 30 by increasing the delay described above. If the average test package length is too small, it is necessary to increase the size of the $A_3$ segment of the last lest package inserted into the analytical line 30 by decreasing the delay described above.

As noted above, in the preferred embodiment of the present invention, not every measured length is used to calculate Taver. Instead, only the measured lengths of those test packages that satisfy certain criteria are used. The particular criteria used can vary. One example is to use only test packages whose $S_1/R_1$ and $R_2$ segments have merged in the vanish zone 50, so-called "merged" packages. Another example is to use only test packages whose $S_1/R_1$ and $R_2$ segments have not yet merged in the vanish zone 50, so-called "non-merged" packages. It will be appreciated by one of skill in the art that in order to accurately identify a test package as "merged" or "non-merged", it will be necessary to use an appropriate pattern recognition protocol and that such a protocol requires that the test package be moving at a uniform, predetermined velocity. If it is determined that the test package is not moving at the uniform, predetermined velocity, then the test package cannot be identified and will thus not be used in the calculation of Taver. As will be apparent to one of skill in the art, one way of determining whether the test package is moving at the uniform, predetermined velocity is to measure the ratio of the transit times of two adjacent liquid segments within the test package and then compare that ratio to an expected value for test packages moving at the uniform, predetermined velocity.

Another criteria that can be used, and that is in fact used in a preferred embodiment of the present invention, is to check whether the measured length of each test package falls within the range of an upper limit and a lower limit. This test thus checks whether each measured length is a reasonable, expected value, and results in only reasonable measurements being used in the calculation of Taver. Based on empirical data, it has been determined that the preferred upper limit is 300 milliseconds and the preferred lower limit is 160 milliseconds. If the measured length in terms of transit time falls outside of this range, it will not be used to calculate Taver.

In a preferred embodiment of the present invention which utilizes the particular criteria just described, typically nine "merged" test packages are used to calculate Taver. It should be understood, however, that other appropriate criteria can be used to determine which test package lengths are used to calculate Taver without departing from the scope of the present invention. For example, both "merged" and "non-merged" test packages could be used.

According to an aspect of the present invention, the delay for the chemistry feedback loop is calculated according to the following equation:

$$Delay = CP - Error * K,$$

wherein CP is as described above with respect to the immunoassay feedback loop, Error equals Tset−Taver, and K is a gain factor. In a preferred embodiment of the present invention, Tset equals 220 milliseconds and K equals 0.5.

While in the preferred embodiments described herein only the proportional element of control is used, it will be apparent to one of skill in the art that the integral or differential elements of control could also be used.

All of the necessary control for the system components described above is provided by appropriate software loaded into the data acquisition computer. The details and particular implementations of the software would be readily apparent to one of skill in the art based on the functions described above and thus will not be repeated herein.

One skilled in the art will appreciate that the present invention can be practiced by other than the described embodiments, which are presented for purposes of illustration and not of limitation.

We claim:

1. An apparatus for controlling a stream of liquid packages, each liquid package comprising a plurality of liquid and air segments, the apparatus comprising:

a first and second fluid conduit each being internally coated with an isolation liquid;

a probe for selectively aspirating liquid segments and air segments into the first fluid conduit in a plurality of cycles, each cycle ending with the aspiration of a final liquid segment and a final air segment in that order said liquid segments each occupying a length of said first and second fluid conduits wherein the length occupied by each liquid segment is dependent upon the surface tension of the liquid comprising the segment, a valve coupled to said first fluid conduit and said second fluid conduit, said valve being adapted to be actuated between a first position in which said second fluid conduit is coupled to said first fluid conduit and a second position in which said second fluid conduit is not coupled to said first fluid conduit;

an air and liquid interface detector positioned along said second fluid conduit a fixed distance from said valve, said fixed distance corresponding to a predetermined fixed volume within said second fluid conduit; and a means for stopping the aspiration of the final air segment in a current cycle when said air and liquid interface detector detects an interface between an air segment and a liquid segment of a previous cycle which have moved into said second fluid conduit after the final liquid segment of said previous cycle has fully entered said second fluid conduit and for actuating said valve from said first position to said second position at a time subsequent to said detection;

wherein stopping the aspiration of the final air segment in a current cycle controls the length of the liquid segments in the previous and current cycle ensuring that the liquid and air segments of the previous cycle are at a desired distance from the valve before the valve is actuated, and wherein each of said cycles begins with the aspiration of a first air segment and a first liquid segment in that order, the apparatus further comprising:

a third fluid conduit being internally coated with an isolation liquid into which the liquid and air segments aspirated in each of said cycles are inserted and in which the stream of liquid packages is repeatedly bi-directionally flowed in a forward and a reverse direction, said third fluid conduit being coupled to said valve such that when said valve is in said second position said third fluid conduit is coupled to said second fluid conduit;

a second air and liquid interface detector positioned along said third fluid conduit adjacent said valve; and means for stopping said flow of said stream of liquid packages in said reverse direction at a point in time when said second air and liquid interface detector detects an interface between the first air segment and the first liquid segment most recently inserted into said third fluid conduit adjusted by a delay, said delay being normalized around a predetermined nominal center point delay according to a feedback loop.

2. An apparatus according to claim 1, wherein said valve comprises a shear valve.

3. An apparatus according to claim 1, wherein said air and liquid interface detector comprises a bubble detector.

4. An apparatus according to claim 1, said feedback loop being based upon a time differential TD equal to $T_2-T_1$, wherein $T_1$ is a time at which a first particular liquid segment of a particular liquid package reaches a reference during said flow of said stream in said forward direction and $T_2$ is a time at which a second particular liquid segment of said particular liquid package reaches said reference during said flow of said stream in said reverse direction.

5. An apparatus according to claim 4, said delay being calculated according to the following formula:

$$\text{Delay} = CP - \text{Error} * K,$$

wherein CP is said predetermined nominal center point delay, Error is equal to a predetermined set point minus TD, and K is a gain factor.

6. An apparatus according to claim 4, wherein said reference point comprises a third air and liquid interface detector positioned along said third fluid conduit.

7. An apparatus according to claim 1, wherein the liquid and air segments aspirated in each of said cycles and inserted into said third fluid conduit each comprise a liquid package having a length, wherein said length is measured for a plurality of said liquid packages during said flow of said stream in either said forward or said reverse direction and wherein an average length is calculated using a plurality of said measured lengths, said feedback loop being based upon a difference between a target liquid package length and said average length.

8. An apparatus according to claim 7, said delay being calculated according to the following formula:

$$\text{Delay} = CP - \text{Error} * K,$$

wherein CP is said predetermined nominal center point delay, Error is equal to said target liquid package length minus said average length, and K is a gain factor.

9. A method for controlling a stream of liquid packages, each liquid package comprising a plurality of liquid and air segments, the method comprising:

selectively aspirating liquid segments and air segments into a first fluid conduit in a plurality of cycles, each liquid segment occupying a length of the first and second fluid conduits which length is dependent upon the surface tension of the liquid in each segment, each cycle ending with the aspiration of a final liquid segment and a final air segment in that order, said first fluid conduit being coupled to a valve, said valve being coupled to a second fluid conduit, wherein said valve is adapted to be actuated between a first position in which said first fluid conduit is coupled to said second fluid conduit and a second position in which said first fluid conduit is not coupled to said second fluid conduit;

detecting an interface between an air segment and a liquid segment of a previous cycle which have moved into said second fluid conduit at a position along said second fluid conduit which is a fixed distance form said valve after the final liquid segment of said previous cycle has fully entered said second fluid conduit, said fixed distance corresponding to a predetermined fixed volume within said second fluid conduit; and stopping the aspiration of the final air segment in a current cycle when said interface has been detected so as to ensure that the liquid and air segment of a previous cycle have moved the fixed distance from the valve:

and actuating said valve from said first position to said second position at a time subsequent to said detection, wherein each of said cycles begins with the aspiration of a first air segment and a first liquid segment in that order, the method further comprising:

inserting the liquid segments and the air segments aspirated in each of said cycles into a third fluid conduit such that for each of said cycles the first liquid segment and the first air segment are the next-to-last and the last liquid and air segment, respectively, inserted;

flowing said stream of liquid packages in a forward direction and a reverse direction in said third fluid conduit said third fluid conduit being coupled to said valve such that when said valve is in said second position said third fluid conduit is coupled to said second fluid conduit;

detecting an interface between the first air segment and the first liquid segment most recently inserted into said third fluid conduit at a reference location along said third fluid conduit adjacent said valve when said stream is flowing in said reverse direction; and stopping said flow of said stream at a point in time when said interface is detected adjusted by a delay, said delay being normalized around a predetermined nominal center point delay according to a feedback loop.

10. A method according to claim 9, further comprising actuating said valve after said flow of said stream is stopped.

11. A method according to claim 9, wherein said valve comprises a shear valve.

12. A method according to claim 9, said feedback loop being based upon a time difference TD equal to $T_2-T_1$, wherein $T_1$ is a time at which a first particular liquid segment of a particular liquid package reaches a reference point during said flow of said stream in said forward direction and $T_2$ is a time at which a second particular liquid segment of said particular liquid package reaches said reference point during said flow of said stream in said reverse direction.

13. A method according to claim 12, said delay being calculated according to the following formula:

$$\text{Delay} = CP - \text{Error} * K,$$

wherein CP is said predetermined nominal center point delay, Error is equal to a predetermined set point minus TD, and K is a gain factor.

14. A method according to claim 9, wherein said detecting step is performed using an air and liquid interface detector positioned at said reference location.

15. A method according to claim 9, wherein the liquid and air segments aspirated in each of said cycles and inserted into said third fluid conduit each comprise a liquid package having a length, wherein said length is measured for a plurality of said liquid packages during said flow of said stream in either said forward or said reverse direction and wherein an average length is calculated using a plurality of said measured lengths, said feedback loop being based upon a difference between a target liquid package length and said average length.

16. A method according to claim 15, said delay being calculated according to the following formula:

$$\text{Delay} = CP - \text{Error} * K,$$

wherein CP is said predetermined nominal center point delay, Error is equal to said target liquid package length minus said average length, and K is a gain factor.

* * * * *